United States Patent [19]

Stabinsky

[11] Patent Number: 4,739,044
[45] Date of Patent: Apr. 19, 1988

[54] METHOD FOR DERIVITIZATION OF POLYNUCLEOTIDES

[75] Inventor: Yitzhak Stabinsky, Boulder, Colo.

[73] Assignee: Amgen, Thousand Oaks, Calif.

[21] Appl. No.: 744,798

[22] Filed: Jun. 13, 1985

[51] Int. Cl.$^4$ .................. C07H 15/12; C07H 17/00
[52] U.S. Cl. ........................... 536/27; 536/28; 536/29
[58] Field of Search ................. 536/27, 28, 29

[56] References Cited

U.S. PATENT DOCUMENTS

| | | | |
|---|---|---|---|
| 4,310,662 | 1/1982 | Crea | 536/27 |
| 4,415,732 | 11/1983 | Caruthers et al. | 536/27 |
| 4,417,046 | 11/1983 | Hsiung | 536/27 |

FOREIGN PATENT DOCUMENTS 063879 11/1982 European Pat. Off.
2125798 3/1984 United Kingdom.

OTHER PUBLICATIONS

Barker, et al., *J. Biol. Chem.*, 22 7135–7147, (1972).
Bauman, et al., *J. Histochem. Cytochem.*, 29, 227–237, (1981).
Broker, et al., *Nucleic Acids Res.*, 5, 363–384, (1978).
Cuatrecasas, *J. Biol. Chem.*, 245 (12), 3059–3065, (1970).
Kempe, et al., *Nucleic Acids Res.*, 13, 45–57, (1985).
Manning, et al., *Chromosoma (Berl)*, 53, 107–117, (1975).
Matteucci, et al., *J. Am. Chem. Soc.*, 103, 3185–3191, (1981).
Richards, et al., *Proc. Natl. Acad. Sci. (U.S.A.)*, 76, 676–680, (1979).
Suggs, et al., in *Developmental Biology Using Purified Genes*, Brown, et al. (eds.), Academic Press, New York, pp. 683–693, (1981).

*Primary Examiner*—J. R. Brown
*Assistant Examiner*—John W. Rollins
*Attorney, Agent, or Firm*—Marshall, O'Toole, Gerstein, Murray & Bicknell

[57] ABSTRACT

A method for the preparation of a 3' end functionalized polynucleotide is disclosed. An amine-functionalized solid phase support is treated sequentially with an anhydride, then with an ω-hydroxylamine. A polynucleotide is chemically synthesized on the treated support and is subsequently cleaved therefrom by hydrolysis of the amide bonds. A polynucleotide having a 3' free primary amine is recovered for use in hybridization assays and other uses.

5 Claims, No Drawings

METHOD FOR DERIVITIZATION OF POLYNUCLEOTIDES

BACKGROUND

The present invention relates in general to the preparation of derivatized polynucleotides. In particular, the present invention relates to the derivatization of the 3' end of synthetic polynucleotides.

The attachment of a functional group to a nucleic acids permits its detection and quantitation. In a hybridization assays a labelled nucleic acid probe is used to search a sample for a target nucleic acid which has a complementary nucleotide sequence. The target is then immobilized by hybridization to a support-bound nucleic acid probe to form a "sandwich". Such a sandwich is detectable as the amount of label bound to the support. Functionalization techniques may be employed both to attach a reactive group for binding the nucleic acid to a reporter group and to bind the nucleic acid to a reactive group on a support. Thus, methods for derivatizing nucleic acids are particularly useful for preparing materials for hybridization assays.

One approach to labelling a probe for use in hybridization assays involves binding a radioisotope (e.g., $^{32}P$, $^{3}H$, or $^{125}I$) to the probe. However, difficulties inherent in the two common methods of detecting radioactive labels limit the usefulness of its approach. One of the common detection techniques, called, autoradiography, is a timeconsuming procedure which relies upon reduction of silver ions to form silver grains in a photographic emulsion. Scintillation counting, the other common detection technique, requires expensive equipment and a certain amount of delay as well. Furthermore, radioisotopes require special handling for safety reasons. Some radioactive isotopes, such as $^{125}I$, have relatively short shelf-lives, which further limit their usefulness in a clinical diagnostic setting.

In non-radioactive labelling systems, a probe is "labelled" with a reporter group and a signal is associated with the reporter group to enable detection. A reporter is an agent which is used to indicate the presence or location of the probe. The signal itself, which is directly perceptible, may be generated by a separate or separable signal molecule. A label is properly a type of reporter which incorporates a signal molecule.

One approach to the attachment of labels to probes is described in Ward, et al., European Patent Application No. 63,879. Ward discloses the preparation of probes having a biotin reporter molecule covalently attached to a purine or pyrimidine ring. Selected biotinylated purines and pyrimidines are then directly incorporated within the phosphodiester backbone of the nucleic acid of the probe by enzymatic means. However, enzymatic techniques are costly and difficult to perform.

Other approaches link a label to a probe by way of a protein. Single-stranded polio virus RNA is naturally linked to a protein which may be reacted with the N-hydroxysuccinimidyl ester of biotin to obtain an RNA probe having a biotinylated reporter group detectable by specific attachment of avidin-coated spheres. Richards, et al., *Proc. Natl. Acad. Sci. (U.S.A.)*, 76: 676–680 (1979). Similarly, biotin-labelled cytochrome c may be coupled to RNA by reaction in the presence of formaldehyde and thereafter labelled with avidin-coated spheres. Manning, et al., *Chromosoma (Berl.)*, 53: 107–117 (1975). Nevertheless, because not all nucleic acids are naturally linked to proteins and because the location and amount of cytochrome c binding to a nucleic acid is not readily predictable, it would be desirable to have a chemical synthetic technique for endlabelling.

In one chemical synthetic technique, nucleic acids are converted to 3'-aldehydes by oxidation and condensed with alkyldiamines or polyamines to provide a reporter group for the attachment of biotin. Broker, et al., *Nucleic Acids Res.*, 5: 363–384 (1978). Similarly, aldehydes generated by the periodate oxidation of nucleic acids may be used to couple fluorescent labels to the nucleic acids. Bauman, et al., *J. Histochem.Cytochem.*, 29: 227–237 (1981). However, it would be desirable to have a technique for attaching reporter groups to polynucleotides bound to a support in an automated process for nucleic acid synthesis.

In yet another approach to 5' labelling, biotin is converted to 2-(biotinylamido)ethanol and condensed to a phosphorylated, polymer-supported nucleotide. The condensation of the aminoethanol derivative of biotin to the 5' hydroxyl group of a ribose ring gives a stable phosphodiester bond upon deprotection of the nucleotide. Kempe, et al., *Nucleic Acids Res.*, 13: 45–57 (1985). Nevertheless, because specific reporter groups are attached, this approach does not teach preparation of an oligonucleotide with a generally reactive functionality which may later be used to attach a variety of desired reporter groups.

Nucleotides in solution have been amine-functionalized by condensation with protected 6-amino-1-hexanol phosphate. Barker, et al., *J. Biol. Chem.*, 22: 7135–7147 (1972). However, these procedures are difficult to perform and have not been integrated with solid-phase synthesis.

In another approach to binding nucleotides to supports for the purification of nucleases by affinity chromatography, single nucleotides, 3'-derivatized with p-aminophenol are attached to a gel matrix by a linker. The linker is formed by attaching 3,3'-diaminodipropylamine to the matrix using cyanogen bromide and azide. The resulting amine-functionalized gel is treated with succinic anhydride and then coupled to the amine-functionalized nucleotide with a carbodiimide. Cuatrecasas, *J. Biol. Chem.*, 12: 3059–3065 (1978). Nevertheless, the manufacture of the amine-functionalized nucleotide itself is performed in solution by tedious procedures. See e.g., Barker et al, *J. Biol. Chem.*, 22, 7135–7147 (1972).

Therefore, there is a need for a method and composition for the generic attachment of reporter groups to polynucleotides undergoing solid phase synthesis.

BRIEF SUMMARY

Accordingly, the present invention provides a method for the preparation of a manufactured nucleic acid having a 3' functionalized end. As a first step in the method, a carboxylic acid functionalized solid phase support is used or an amine functionalized solid phase support is treated with a selected anhydride or reacted with a molecule containing carboxyl moieties at either end, thereby forming an amide bond between the support and the anhydride residue, and forming a carboxylic acid function thereon.

The second step in the method of the present invention involves coupling the product of the first step with a selected hydroxylamine linker in the presence of a coupling agent. The product of the second step is a polymeric support having two amide bonds (where an amine-functionalized bead is used) and a free hydroxyl group.

The third step of the method of the present invention involves chemical synthesis of a polynucleotide chain or the support starting from the free hydroxyl group and generating a phosphoester bond between the linker and the nucleic acid.

After the completion of the polynucleotide synthesis on the support, the polynucleotide with a 3' primary amine function is hydrolyzed from the support by treating the product of the third step of the method with a solution containing ammonia.

DETAILED DESCRIPTION OF THE PREFERRED EMBODIMENT

In a preferred method according to the present invention, an amino group is attached to the 3' end of a polynucleotide during synthesis. The solid phase support may be porous or non-porous, i.e. a polymeric support such as controlled pore glass, silica gel, polystyrene, agarose or sephadex. It is also possible, although not optimal, to utilize supports such as nitrocellulose paper. The support preferably carries an amine function, although carboxylic acid groups may be employed.

The amine-functionalized solid support is treated with an anhydride, such as succinic anhydride or pyrimidinic anhydride. The presently most preferred anhydride is phthallic anhydride, due to the ease with which it may be removed by hydrolysis and due to the symmetrical nature of the amide bonds which it forms.

Although it is convenient to use anhydrides, one may also use any molecule which contains two terminal carboxylic acid moieties, activate these groups with p-nitrophenol and dicyclohexylcarbodiimide (DCC) or with NHS and then condense the resulting molecule with the solid support.

Among the compounds suitable for use as linkers in the condensation reaction agent are ω-hydroxylamines including straight chain amino alcohols having a terminal amino group and a terminal hydroxide group. It is desirable in this step that the carbon atoms in the chain not exceed ten, and preferably are within the range of 1 to 6. Such amino alcohols include methanolamine, ethanolamine, propanolamine, butanolamine, pentanolamine, hexanolamine, heptanolamine, octanolamine, nonanolamine and decanolamine. However, in principle, any molecule having hydroxyl and amine group available for respectively forming a bond with a polynucleotide and with a carboxyl-functionalized support may be employed. For example, a polylysine chain may, after reduction of its carboxyl function, be used so long as only those amine groups which are to be bonded to the support are exposed while all others are protected by appropriate blocking groups. Similarly, it is desirable to block other reactive groups which would otherwise compete with or interfere with the formation of the amide bond between the linker molecule and the support.

Chemical synthetic methods for polynucleotide generation which may be employed according to the present invention include triester synthesis; the phosphate triester procedure; solid phase synthetic methods employing tetrazolide derivatives and nucleoside phosphates; and the phosphoramidite methods described in U.K. Patent Application No. GB2,125,798 published Mar. 14, 1984 and in Caruthers, et al., U.S. Pat. No. 4,415,732.

Treatment of the support-bound nucleic acid sequence with an ammonia solution causes hydrolysis of the amide bonds developed above, thereby releasing into solution a free manufactured oligonucleotide having on its 3' end an alkyl chain with a free primary amine function. Once the oligonucleotide is recovered from solution, the free amine function is readily available for attachment of a reporter group.

The method of the present invention is illustrated in detail by the following illustrative examples, which describe the steps of the synthesis of 3' primary amine-functionalized oligonucleotides.

EXAMPLE 1

500 mg of controlled pore glass with an amine function (available from Pierce Chemical Company, Rockland, Ill.) containing 50 micromoles of amino groups was reacted for 30 minutes at room temperature with 250 mg (1 mole) of either phthallic anhydride, succinic anhydride or pyridinic anhydride in the presence of 2 ml anhydrous pyridine and 61 mg 4-dimethyl amino pyridine. The resulting polymers were thereafter rinsed with methylene dichloride, ethyl alcohol and ether, and dried.

Each polymer (450 mg or 45 μmoles) was then reacted in solution with 1.5 ml methylene dichloride and 330 mg decyclohexylcarbodiimide (DCC) for 30 minutes at room temperature. The solution above the bead was decanted and replaced with a solution of 6-amino-1-hexanol (117 mg/1 mole) in 2 ml methylene dichloride and left at room temperature for approximately 8 hours. Following similar procedures, another 450 mg of each activated polymer was placed in solution, and after decanting, the bead was reacted with a solution of 1 mole hexanolamine in 2 ml methylene dichloride under equivalent conditions.

The six hydroxy-functionalized esters thus obtained from solution were the following:

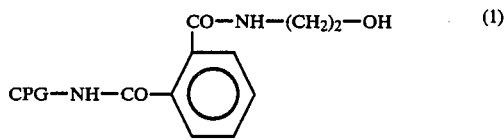
(1)

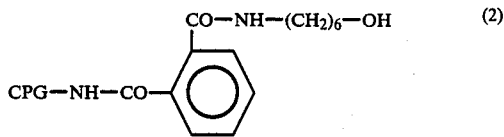
(2)

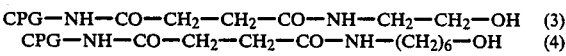

CPG—NH—CO—CH₂—CH₂—CO—NH—CH₂—CH₂—OH (3)
CPG—NH—CO—CH₂—CH₂—CO—NH—(CH₂)₆—OH (4)

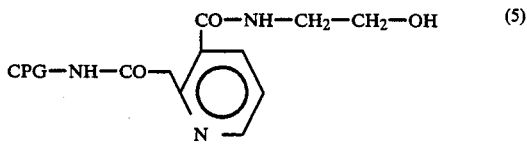
(5)

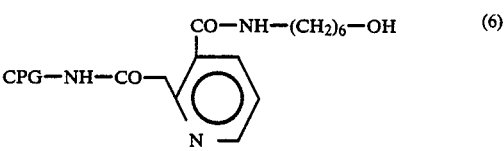
(6)

While each hydroxy-methyl ester could be employed as a support on which to synthesize an oligonucleotide, only supports 1, 2, 3 and 5 were selected for such use. Employing the phosphoramidite method of oligonucleotide chain extension see [Caruthers, U.S. Pat. No. 4,415,732], a chain of deoxythymidines having 3' ends blocked with dimethoxytrityl groups was synthesized on each support through the active hydroxy group thereon.

When 13 thymidines were incorporated in the polynucleotide by these procedures, the amide bonds with the support were hydrolyzed, thereby releasing free oligonucleotides having 3' free primary amine groups. Consequently, 40 mg of each supported chain containing 37 to 40 μmoles of dimetroxytrityl (DMTr) groups per gram were treated with concentrated $NH_4OH$ (2 ml per 40 mg) at room temperature. Thereafter, 100 μl of each solution was removed and dried. To follow the rate of peptide bond hydrolysis by this treatment, 0.1 M p-toluenesulfonic acid was added to the dried material and the DMTr groups were quantitated by spectrophotometry at 498 nm.

At room temperature, the hydrolyses of the amide bonds in each solution (i.e., the release of DMTr-DNA to solution) was determined and the results reported in Table I below.

TABLE I

| Time | Support/Bond | % Hydrolysis |
| --- | --- | --- |
| 18 hours | 1/phthallic amide bond | 57% |
| 18 hours | 2/phthallic amide bond | 57% |
| 18 hours | 3/succinic amide bond | 23% |
| 18 hours | 5/pyridinic amide bond | 63% |
| 42 hours | 1/phthallic amide bond | 92% |
| 42 hours | 2/phthallic amide bond | 92% |
| 42 hours | 3/succinic amide bond | 53% |
| 42 hours | 5/pyridinic amide bond | ~100% |

The results indicated that optimal release of the 3' functionalized oligonucleotides into solution occurs where the anhydride employed in the method of the present invention permits the development of symmetrical amide bonds in the support.

In the following example the efficiency of the method according to the present invention is examined.

EXAMPLE 2

In order to test the efficiency of the 3'-functionalization of oligodeoxynucleotides through synthesis on a derivatized solid support, a deoxyoligonucleotide having the following sequence:

5'  
HO—AACAACTCCCTAACCCCTGCTTTTTAAAGAC (7)

was synthesized chemically on 40 mg. (about 2 μmoles) of each of supports (8) and (9):

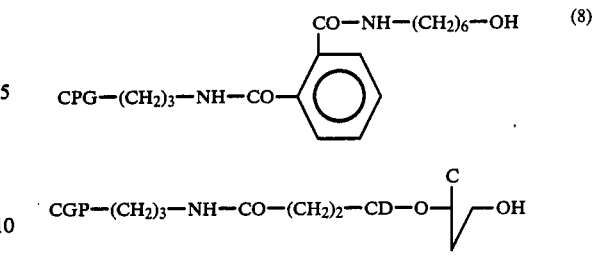

Chemical synthesis was carried out by the solid phase phosphite approach (Caruthers et al, U.S. Pat. No. 4,415,732) using 5'-dimethoxytrityl-3' methoxy, NN'-dimethylaminophosphoramidites in the condensation reactions. In the first synthetic cycle on solid support (8), 5'-dimethoxytrityl-deoxycytidyl-3'-methoxy-NN'-dimethylaminophoshoramidite was used, and from there on the synthetic cycles on the two supports were identical. Following the last cycle, the dimethoxytrityl groups were removed from the DNA and the two oligodeoxynucleotides were removed from the supports using 2 ml of 15M $NH_4OH$ at 30° C. for 18 hours and then deprotected [Matteucci et al, *J. Am. Chem. Soc.,* 103, 3185–3191 (1981)].

The oligodeoxynucleotides were purified by electrophoresis on a 12% polyacrylamide gel run under denaturing conditions (7M Urea). The slowest migrating band from each lane (corresponding to more than 90% of the total U.V. absorbing material) was cut from the gel. The two oligodeoxynucleotides were extracted from the gel and desalted on 10 ml Sephadex G50/40 (Sigma) columns using 10 mM triethylammonium bicarbonate, pH 7.0. The oligodeoxynucleotides were quantitated spectrophotometrically and lyophilized.

Analysis of the products by analytical polyacrylamide gel electrophoresis showed that the products to be homogenous and that the deoxyoligonucleotide obtained from support (8) migrated with a significantly slower mobility than the deoxyoligonucleotide from support (9). The formula of the deoxyoligonucleotide obtained from support (8) was confirmed to be:

and that obtained from support (9) had the same deoxynucleotide sequence but was missing the 3'-tail of the first deoxynucleotide.

The yields of the recovered products, after the purification step were as follows:

From 40 mg (1.95 μmoles) of support (8) 26.4 $A_{260}$ Units of the 3' end-functionalized oligodeoxy-nucleotide were obtained, while only 18.6 $A_{260}$ units of the 3'-OH oligodeoxynucleotide were obtained from 40 mg (2.1 μmoles) of support (9).

In the following example, a 3'-fluorescein-labelled oligonucleotide is prepared.

TABLE II

| | Deoxynucleotide Composition | | |
| --- | --- | --- | --- |
| | | $\epsilon_{260}/\epsilon_{280}$ | |
| | | Calculated | Found |
| 3'-functionalized deoxynucleotide | $A_{10}C_{11}G_2T_8$ | 1.85 | 1.84 |

TABLE II-continued

| Deoxynucleotide Composition | | | |
|---|---|---|---|
| | | $\epsilon^{260}/\epsilon^{280}$ | |
| | | Calculated | Found |
| 3'-oit deoxyoligo-nucleotide | $A_{10}C_{11}G_2T_8$ | 1.85 | 1.82 |

EXAMPLE 3

A 3'-amine oligodeoxynucleotide was prepared according to the procedure of Example 1. Another oligodeoxynucleotide was prepared which was identical to the first, but which incorporated a $^{32}P$ label as well and which had a specific activity of 1540 cpm/fm. To 2.95 nmoles of the $^{32}P$-labelled oligodeoxynucleotide in 17 μl of 100 mM sodium carbonate buffer was added 17 μmoles of 25 mM fluorescein isothiocyanate (Aldrich Chemical Co., Milwaukee, Wis.) in DMSO. This solution was vortexed and incubated for 1 hour at 37° C. An additional 17 μl of carbonate buffer and 17 μl of fluorescein isothiocyanate solution were added. After 2 hours at 37° C., the oligodeoxynucleotide was ethanol precipitated and purified by electrophoresis on a 6 M urea, 15% polyacrylamide gel.

The product was identified by autoradiography, the appropriate band was isolated, eluted and gel filtered on a Sephadex G50/50 column using 10 mM triethylammonium bicarbonate (TEAB) as the eluent. The product was isolated in 30% yield (0.75 μmoles).

Analysis of the product by analytical polyacrylamide gel electrophoresis and autoradiography showed the product to be homogenous and to migrate with a characteristically slower mobility than the starting material.

Analysis of the product by UV spectroscopy revealed it to have the correct spectral properties for the fluoresceinfunctionalized deoxyoligonucleotide which were:

$A_m = 26.36 \times 10^4$ $A^{260} = 0.20$ $A^{260}/A^{280} = 1.86$ $A_m(\text{fluorescein}) = 7.5 \times 10^4$ $A^{495} = 0.06$ In the following example a 3'-biotin-labelled oligodeoxynucleotide was prepared.

EXAMPLE 4

To 200 picomoles of an unlabelled 3' amine nucleic acid and 40 μmoles of 100 mM sodium bicarbonate buffer, pH 8.3, was added 40 μmoles of biotin-N-hydroxysuccinimide estes solution (10 mg/ml in DMSO). This solution was vortexed and incubated at 25° C. for 30 minutes. An additional 40 μl of bicarbonate buffer and 40 μl of biotin-N-hydroxysuccinimide ester solution were then added.

After 30 minutes, the product was ethanol precipitated and purified by electrophoresis on a 6 molar urea20% polyacrylamide gel. The appropriate band was identified by autoradiography, isolated, gel eluted, and gel filtered on a Sephadex G50/50 column. The product was isolated in 40% yield, as analyzed by radioactive labelling, and was shown to be homogenous on a 20% analytical polyacrylamide gel.

The following example demonstrates hybridization of a 3'-modified oligonucleotide to a complementary target DNA bound to a nitrocellulose filter.

EXAMPLE 5

In order to test the effect of modifying a nucleic acid at the 3' position and to test the effect of further functionalization, with biotin or fluorescein, for example, $^{32}P$-labelled 3' amine polynucleotides (synthesized as above) were hybridized to complementary target DNA attached to nitrocellulose. These hybridization complexes were then subjected to increasingly more stringent wash conditions in order to determine the effect of 3' modification according to the present invention on the hybridization availability of these nucleic acid sequences.

Specifically, 20 μg of a plasmid pUC18sac-1 was linearized by digestion with the restriction enzyme HindIII. Aliquots (2 μl ) containing 1 μg of linearized plasmid DNA were spotted onto nitrocellulose filters. This DNA was denatured by soaking the nitrocellulose filter in 0.5 M NaOH, 1.5 M NaCl saturated on a 3 MM Whatman paper. This material was then neutralized by exposure to 3 MM Whatman paper saturated with 1.5 M NaCl, 0.5 M Tris, pH 8.0, and then transferred to 3 MM Whatman paper saturated with 2×SSPE.

The nitrocellulose was then air-dried for 30 minutes and baked for 2 hours at 80° C. Pre-hybridization was carried out for 3 hours at 50° C. in 5×SSPE and 0.2% each of bovine serum albumin, Ficoll, and polyvinyl pyrrolidone. Hybridization was accomplished by incubation of the nitrocellulose in 2 ml of 5×SSPE solution containing 1 picomole of $^{32}P$-polynucleotide probe, 200 μg of denatured placental DNA, and 0.2% each of bovine serum albumin, Ficoll, and polyvinyl pyrrolidone, and 0.2% SDS for 15 hours at 50° C. The nitrocellulose was then washed three times in 6×SSC for 5 minutes at 25° C. at various temperatures as shown in Table II. Radioactivity retained on the filter was assayed by liquid scintillation counting. The temperature at which 50% of the hybridization probe was retained was determined to be the melting temperature of that nucleic acid.

TABLE III

| Temperature (°C.) | % Hybridization |
|---|---|
| 3' Fluorescein-labelled Nucleic Acid | |
| 60 | 100 |
| 65 | 96 |
| 70 | 76 |
| 75 | 30 |
| 80 | 16 |
| 3' Amine Nucleic Acid | |
| 60 | 100 |
| 65 | 70 |
| 70 | 44 |
| 75 | 13 |
| 80 | 2 |

The theoretical melting temperature $T_m$ for the following nucleic acids is 78%. Suggs, et al., in *Developmental Biology Using Purified Genes*, Brown, et al. (eds.), Academic Press, New York, pages 683–693 (1981).

TABLE IV

| | $T_m$ |
|---|---|
| 3' fluorescein-labelled nucleotide | 72° C. |

TABLE IV-continued

| | $T_m$ |
|---|---|
| 3' amine nucleic acid | 67° C. |

By comparison of Tables III and IV, it may be readily determined that the 3' modification of nucleic acids has little, if any, effect on their hybridization $T_m$.

Numerous modifications and variations in the invention are expected to occur to those skilled in the art upon consideration of the foregoing description. For example, the use of a polylysine having a reduced carboxyl group as the hydroxylamine permits the attachment of multiple reporter groups (i.e. at a plurality of the amine groups of the polylysine moiety) to the polynucleotide. Consequently, only such limitations as appear in the appended claims should be placed on the invention.

What is claimed is:

1. A method for preparing a functionalized polynucleotide comprising the steps of:

forming an amide bond between a support-bound carboxyl group and an amino group of a hydroxylamine linker molecule;

initiating synthesis of a polynucleotide on the hydroxyl group of the hydroxylamine linker molecule;

hydrolyzing the amide bound between the amine and the support-bound carboxyl group; and recovering the polynucleotide connected to the amine group by way of the linker molecule.

2. The method according to claim 1 wherein said polynucleotide sequence is a deoxyribonucleic acid sequence.

3. The method according to claim 1 wherein said polynucleotide sequence is a ribonucleic acid sequence.

4. The method according to claim 1 wherein said hydroxylamine contains from 1 to 10 carbon atoms.

5. The method according to claim 4 wherein said hydroxylamine is selected from the group comprising methanolamine, ethanolamine, propanolamine, butanolamine, pentanolamine, hexanolamine, heptanolamine, octanolamine, nonanolamine and decanolamine.

* * * * *

UNITED STATES PATENT AND TRADEMARK OFFICE
CERTIFICATE OF CORRECTION

PATENT NO. : 4,739,044
DATED : April 19, 1988
INVENTOR(S) : Yitzhak Stabinsky

It is certified that error appears in the above-identified patent and that said Letters Patent is hereby corrected as shown below:

In the Specification at column 5, line 5, delete "[" before "Caruthers" and insert --[-- before "see".

In column 7, line 63 delete "urea20%" and substitute --urea-20%-- therefor.

Signed and Sealed this

Second Day of May, 1989

Attest:

DONALD J. QUIGG

Attesting Officer

Commissioner of Patents and Trademarks